United States Patent [19]

Gonzalez

[11] Patent Number: 5,232,456
[45] Date of Patent: Aug. 3, 1993

[54] PROTECTOR FOR SELF-RETRACTILE HYPODERMIC NEEDLES

[76] Inventor: Antonio S. Gonzalez, Riu Canyoles 6., 46900 El Vedat De Torrent (Valencia), Spain

[21] Appl. No.: 887,287
[22] Filed: May 22, 1992
[51] Int. Cl.⁵ .............................................. A61M 5/32
[52] U.S. Cl. ..................................... 604/192; 604/198; 604/263
[58] Field of Search ............... 604/263, 198, 195, 192, 604/110, 187, 232

[56] References Cited

U.S. PATENT DOCUMENTS

| | | | |
|---|---|---|---|
| 4,767,413 | 8/1988 | Haber et al. | 604/232 X |
| 4,946,446 | 8/1990 | Vadher | 604/198 |
| 4,955,868 | 9/1990 | Klein | 604/198 |
| 5,104,384 | 4/1992 | Parry . | |

*Primary Examiner*—John D. Yasko
*Attorney, Agent, or Firm*—Harris Zimmerman

[57] ABSTRACT

A protector for self-retractile hypodermic needles, the purpose of which is to hide and protect the needle used in injections, both before and after its use. Its basic features are a tubular body opened on both ends and cylindrical, at least inside, including an inner ring-shaped projection with minimum width and thickness, which holds the needle-holder. The body includes as well an expansion spring placed between the end projection of the needle-holder provided to be held against the inner projection of the tubular body, and the strangled front end of the latter. The spring pushes the needle-holder in, hiding the needle, once the syringe has been used for an injection. The tubular body is provided with elongated side windows to simultaneously hold both the tubular body and the syringe during use.

7 Claims, 1 Drawing Sheet

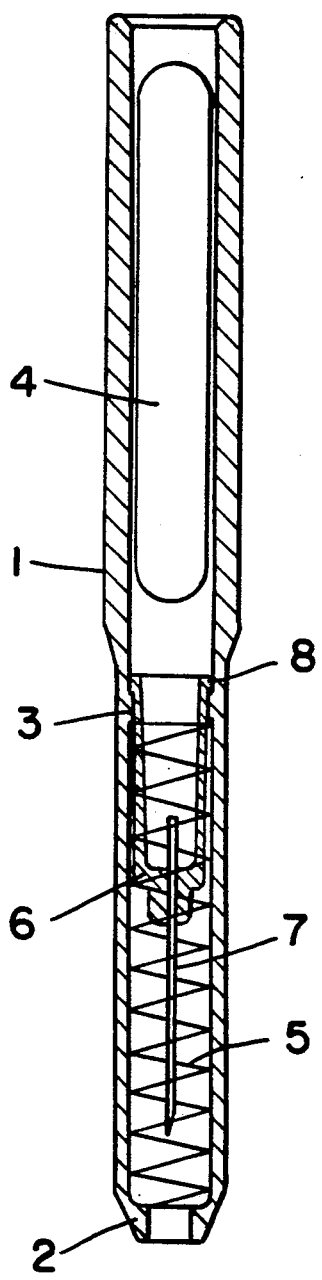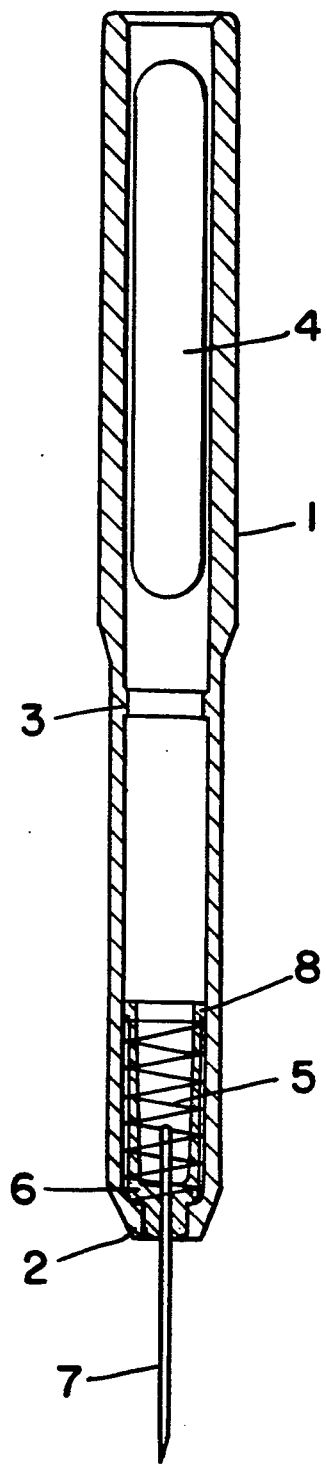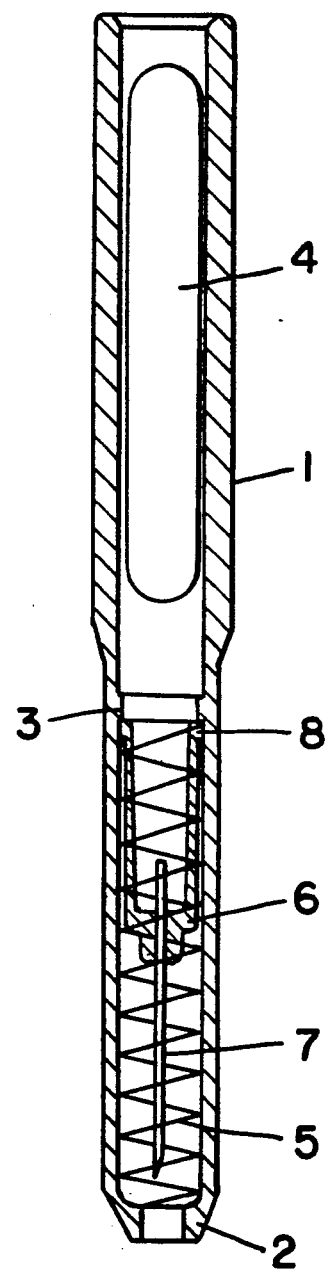
FIG_1   FIG_2   FIG_3

PROTECTOR FOR SELF-RETRACTILE HYPODERMIC NEEDLES

This invention consists of a protector for self-retractile hypodermic needles. It aims at providing the market and general public with a new item which prevents any contact with the hypodermic needle, both before and after use, as well as preventing any accidental pricks with syringes left lying on the ground.

This protector is designed to optionally have a built-in needle-holder with its needle. It has an inner cylindrical and hollow form, with elongated side windows and a small ring-shaped inner projection—placed in front of its middle length. The width of this projection is small and it acts as an anchorage for the needle-holder, which is kept in place by means of a complementary groove on its back end, that is, the end opposite the one where the needle is emerging. It is provided as well with an inner expansion spring situated between the aforementioned ring-shaped projection and the front end of the cylindrical body.

Anchorage for the needle-holder over this projection of the protector is such that a minimum push is enough to free it, thus moving the needle-holder and allowing the needle to emerge at the require moment, to be immediately pushed back by the action of the aforementioned expansion spring. In addition to the described functions, the protector obviously allows the corresponding syringe to be inserted. This will move axially along the protector until its end is fitted on to the needle-holder. At this moment, if one continues to push, the needle-holder will disengage itself, as previously explained, and will move outwards. Then the needle will emerge ready for use first to suction the medicine through its piston and then to inject it. Once this operation is completed, the syringe is pulled back, the needle-holder being also pushed back by the spring and concealing the needle in the process.

The purpose of the elongated side windows with which the protector is provided is to be able to hold at the same time both protector and syringe whenever the syringe is inside.

For a better understanding of the features of this invention, here follows a detailed description referring to the sheet of drawings attached as an integral part of this description, for guidance only. The following items are shown in the said FIGURES:

FIG. 1 shows a longitudinal section of the protector together with the retracted needle-holder and the hidden needle.

FIG. 2 shows a longitudinal section of the same protector with the needle-holder pushed back and the emerging needle.

FIG. 3 shows the hidden position of the needle and needle-holder after use.

Numbers in these figures refer to the following parts:
1. Protector body.
2. Strangled end of the body. (1)
3. Inner ring-shaped projection of the body (1).
4. Side windows of the body. (1)
5. Expansion spring.
6. Needle-holder.
7. Needle.
8. End projection of the needle-holder (6).

As can be seen in these figures, the protector herein described consists of a cylindrical body (1), hollow and opened at both ends, with the end regarded as front end showing a narrowing (2).

This body (1) of the protector shows inside a ring-shaped projections (3) of minimum thickness and small width, which is placed a little ahead of its medium length. The backward portion from the projection area (3) shows some elongated windows (4). An expansion spring (5) is placed inside, between the ring-shaped projection (3) and the narrowed or strangled end (2).

The protector thus formed can be marketed in this configuration or with a built-in needle-holder (6) and the needle itself (7). The needle-holder (6) includes in its back end a ring-shaped projection (8) to hold it against the ring-shaped projections (3) of the protector, so that the needle-holder (6) will be held in this position with the needle (7) completely hidden and protected, as shown in FIG. 1.

When using it, the injection syringe will be axially inserted through the back end of the protector (1), until fitting on to the end mouthpiece of the said syringe in the needle-holder (6). Then, if the syringe continues to be pushed, the projections (8) of the needle-holder (6) will go beyond the projection (3) of the protector, both the former and the needle (7) being pushed until the needle emerges, as shown in FIG. 2, overcoming the spring resistance (5).

In this position the medicine to be injected can be suctioned through the syringe piston. This operation is possible without the syringe or the needle-holder (6) moving backwards, since the user will be holding the syringe through the windows (4) whilst holding the protector (1).

Once the medicine has been injected, the syringe is pushed back and drawn from the protector. At the same time, the spring (5) will cause the needle-holder (6) to retract and therefore the needle (7) to hide again, the needle-holder (6) being held when its end projection (8) is fitted on to the lower step of the projection (3) belonging to the protector.

I claim:

1. A protector for a self-retractile hypodermic needle for use with a conventional syringe, including:

a tubular protector body having a proximal end and a distal end, said tubular protector body having a bore extending continuously therethrough from proximal end to distal end, a narrow outlet opening at said distal end and an open proximal end, a needle holder disposed within said tubular protector body, including a generally cylindrical member having a proximal end and a distal end, said cylindrical member having a closed distal end and an open proximal end, said open proximal end comprising a receptacle for receiving the output end of a conventional syringe, a needle extending through said closed distal end to said receptacle in coaxial alignment with said cylindrical member, said cylindrical member dimensioned to be received in said bore of said tubular protector body in freely translating, coaxial alignment, a first annular projection extending radially outwardly from said proximal end of cylindrical member, and a helical expansion spring disposed in said bore of said tubular protector body and extending from said narrow outlet opening to impinge on said first annular projection of said cylindrical member, said spring circumscribing at least a portion of said cylindrical member and resiliently biasing said cylindrical member to retract said needle within said tubular protector body and to permit said distal end of said cylindrical member t impinge on said distal end of said protector body.

2. The protector for a self-retractile hypodermic needle of claim 1, further including anchorage means for securing said needle holder and needle within said bore, including a second annular projection disposed in said bore of said tubular protector body and extending radially into said bore, said second annular projection dimensioned to impinge on said first annular projection of said needle holder and comprise an anchorage for said needle holder.

3. The protector for a self-retractile hypodermic needle of claim 2, wherein said second annular projection is disposed in a medial portion of said bore of said tubular protector body.

4. The protector for a self-retractile hypodermic needle of claim 3, further including means for temporarily securing a conventional syringe inserted into the proximal end of said protector body, including at lest one window opening in said tubular protector body, said window opening disposed between a medial portion and a proximal portion of said tubular body and extending from said bore to the exterior of said tubular protector body to provide tactile access to the conventional syringe.

5. A protector for a self-retractile hypodermic needle for use with a conventional syringe, including;
- a tubular protector body having a proximal end and a distal end, said tubular protector body having a bore extending continuously therethrough from said proximal end to said distal end, a narrow outlet opening at said distal end and an open proximal end,
- a needle holder disposed within said tubular protector body, including a generally cylindrical member having a proximal end and a distal end, said cylindrical member having a closed distal end and an open proximal end, said open proximal end comprising a receptacle for receiving the output end of a convention a syringe, a needle extending through said closed distal end to said receptacle in coaxial alignment with said cylindrical member, said cylindrical member dimensioned to be received in said bore of said tubular protector body in freely translating, coaxial alignment,
- means for anchoring said needle holder within said bore with said needle retracted within said protector body,
- means for resiliently biasing said needle holder to retract within said protector body,
- means for temporarily securing a conventional syringe inserted into said proximal end of said protector body, including at least one window opening in said tubular protector body, said window opening disposed between a medial portion and a proximal portion of said tubular body and extending from said bore to the exterior of said tubular protector body to provide tactile access to the conventional syringe.

6. The protector for a self-retractile hypodermic needle of claim 5, wherein said means for anchoring said needle holder within said bore, including
- a first annular projection extending radially outwardly from said proximal end of said cylindrical member, and
- a second annular projection disposed in said bore of said tubular protector body and extending radially into said bore, said second annular projection dimensioned to impinge on said first annular projection of said needle holder and comprise an anchorage for said needle holder.

7. The protector for a self-retractile hypodermic needle of claim 6, wherein said means for resiliently biasing said needle holder to retract within said protector body includes a helical expansion spring disposed in said bore of said tubular protector body and extending from said narrow outlet opening to impinge on said first annular projection of said cylindrical member, said spring circumscribing at least a portion of said cylindrical member and resiliently biasing said cylindrical member to retract said needle within said tubular protector body.

* * * * *